US008519157B2

(12) United States Patent
Zhan et al.

(10) Patent No.: US 8,519,157 B2
(45) Date of Patent: Aug. 27, 2013

(54) METHOD FOR PRODUCING OF ULTRA-CLEAN AND HIGH-PURITY N-METHYL PYRROLIDONE

(75) Inventors: Jiarong Zhan, Putuo Shanghai (CN); Huiping Mao, Putuo Shanghai (CN); Zheyu Shen, Putuo Shanghai (CN)

(73) Assignee: Shanghai Chemical Reagent Research Institute, Shanghai (CN)

( * ) Notice: Subject to any disclaimer, the term of this patent is extended or adjusted under 35 U.S.C. 154(b) by 275 days.

(21) Appl. No.: 12/916,686

(22) Filed: Nov. 1, 2010

(65) Prior Publication Data

US 2012/0071670 A1   Mar. 22, 2012

(30) Foreign Application Priority Data

Sep. 17, 2010 (CN) .......................... 2010 1 0284457

(51) Int. Cl.
*C07D 207/263* (2006.01)
(52) U.S. Cl.
USPC .......................................... 548/543; 548/555
(58) Field of Classification Search
None
See application file for complete search history.

(56) References Cited

U.S. PATENT DOCUMENTS 4,965,370 A   10/1990   Goetz et al.

FOREIGN PATENT DOCUMENTS

| CN | 101508667 A | * | 8/2009 |
|----|-------------|---|--------|
| EP | 0346086 A2 |   | 12/1989 |
| JP | 06279401 A |   | 10/1994 |
| JP | 08109167 A |   | 4/1996 |

OTHER PUBLICATIONS

CN101508667A (English translation), Aug. 19, 2009.*

* cited by examiner

*Primary Examiner* — Michael Barker
(74) *Attorney, Agent, or Firm* — Duane Morris LLP; J. Rodman Steele, Jr.; Gregory M. Lefkowitz

(57) ABSTRACT

The present invention provides a method for producing of ultra-clean and high-purity N-methyl pyrrolidone through using industrial grade N-methyl pyrrolidone as raw material. After the pretreatment, sorption and dehydration with 4A molecular sieve, twice membrane filtrations are carried out through using β-cyclodextrin composite membrane for the first and 18-crown-6 composite membrane for the second. The filtrate is rectified under vacuum and filtered through using complexant composite microporous membrane to obtain the product. The ultra-clean and high-purity N-methyl pyrrolidone, produced by the method provided by the present invention, is up to the SEMI C8 standard. And the purity of the product is over 99.8%, the moisture content is less than 0.03%, and the content of single metal ion is less than 1 ppb. Comparing to the prior art, the present invention has the advantage such as the stable quality of the product, simple operation, and is suitable for industrial continuous production.

13 Claims, 1 Drawing Sheet

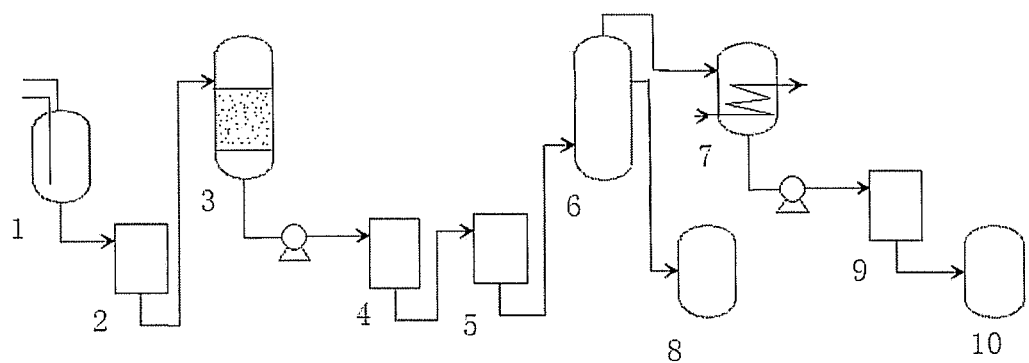

METHOD FOR PRODUCING OF ULTRA-CLEAN AND HIGH-PURITY N-METHYL PYRROLIDONE

FIELD OF THE INVENTION

The invention relates to a production method of ultra-clean and high-purity N-methyl pyrrolidone, specifically to a production method of ultra-clean and high-purity N-methyl pyrrolidone up to the SEMI C8 standard.

BACKGROUND OF THE INVENTION

The N-methyl pyrrolidone (called "NMP" for short), which is nitrogen heterocyclic compound, is one of the important industrial chemicals and widely applied in such fields as petroleum chemical industry, agricultural chemical, medicine and electronic material. The electronic grade N-methyl pyrrolidone can be used widely in the microelectron industry and in the semiconductor industry as the cleansing agent of precision instrument, circuit board photoresist, the solvent for liquid crystal (LCD) material production, the electrode accessory material of lithium battery, and so on. The purity and cleanliness of the N-methyl pyrrolidone have strongly influence on the yield of, the electricity property and the stability of the electronic products. In recent years, with the rapid development of the IT industry, the size of the integrated circuit is smaller and processing speed thereof is higher, and the demand to the purity of the electronic grade chemicals such as electronic grade N-methyl pyrrolidone is higher.

In the prior art, the N-methyl pyrrolidone is obtained through heating, pressurization and dehydration of N-methyl-4-hydroxyl butyrylamide which is produced by the reaction of the .gamma.-butyrolactone as material and methylamine, and this is the only industrial process for producing N-methyl pyrrolidone, and used by corporations such as American GAF, German BASF and the Japanese Mitsubishi and so on for mass production. In further purification process, because the difference between boiling points of the NMP and raw material .gamma.-butyrolactone is only 2° C., it is very difficult to divide the two reagents above by method of rectification. So the multilevel rectification method is commonly used for producing electronic grade reagents.

The U.S. Pat. No. 4,965,370 and the European patent EP346086A2 disclosed the same method for preparing highly purified NMP by adding alkaline metal or alkaline metal salt first into NMP (reacting system) to remove the metal ions, and then several rectifications to high purity NMP. Japanese patent JP06-279401A and JP08-109167A both use repeated distillation to obtain high purity NMP. However, it is difficult to produce NMP on the large scale through using the methods above because of their high cost and high energy consumption, difficult process control and high risk.

SUMMARY OF THE INVENTION

The purpose of the invention is to provide a new method for production of ultra-clean and high-purity N-methyl pyrrolidone to overcome such defects as complex preparing process and difficult process control in prior art.

The conception of the present invention is

Using the industrial grade N-methyl pyrrolidone as raw material, after the pretreatment, sorption and dehydration by the 4A molecular sieve, two membrane filtrations are carried out through using complexant composite membranes with aperture of 0.1 to 0.2 μm. The filtrate is rectified under vacuum and use complexant composite microporous membrane to carry out a third membrane filtration to obtain the target product.

The complexant is the compound which can react with metal ions to form complex ions.

Technical scheme of the present invention is:

The methylamine is fed into the industrial grade N-methyl pyrrolidone to react for about 0.5 to 1.5 hours at temperatures of 5 to 20° C., and the NMP is dehydrated by passing through the 4A molecular sieve with a velocity of flow of 5 to 7 L/min. Two membrane filtrations to the pretreatment fluid are carried out after filtration through complexant composite membranes with the aperture of 0.1 to 0.2 μm. The filtrate is rectified at pressure of 20 to 80 KPa, and the fraction of 80~120° C. is collected from the top of the rectifying tower and filtered through using microporous membrane to get the target product.

The weight ratio between the industrial grade N-methyl pyrrolidone and methylamine is 1:2 to 1:8, preferably of 1:3 to 1:7, the dehydration temperature is controlled at 20 to 40° C.

In the process of rectification, the light fractions are discharged from the outlet at ⅔ height of the rectifying tower with the velocity of flow of 3 to 5 L/min and the fraction of N-methyl pyrrolidone of 80-120° C. is collected from the top opening of the rectifying tower. The fraction collected from the top opening is condensated to obtain the target products at last.

In the present invention, the complexant composite membranes are used for two times of membrane filtration to the pretreatment fluid. Preferably, .beta.-cyclodextrin composite membrane is used for the first filtration and the 18-crown-6 composite membrane for the second.

In the present invention, 18-crown-6 composite membrane is used for the third filtration.

The composite membranes such as β-cyclodextrin composite membranes or 18-crown-6 above can be prepared by following method:

The solid phase Kaolin soil is ground into fine powder of 200 to 300 meshes, and mixed uniformly with the binder (such as polyvinyl alcohol). The mixture is dried at low temperature, sintered at the temperature of 800 to 900° C. The product is cooled down to the room temperature, impregnated and adsorbed by β-cyclodextrin or 18-crown-6 to obtain the composite membranes comprising of solid phase Kaolin soil and complexant, β-cyclodextrin or 18-crown-6 for example, with aperture of 0.1 to 0.2 μm All the reactors in contact with the material in the process and all the pipes used to transfer materials in various procedures are made of high-purity quartz, and the product storing vessel is made of high purity perfluorinated material.

The perfluorinated material is the polymer materials whose hydrogen atoms attached with the carbon atoms are replaced by the fluorine atoms wholly, such as polytetrafluoroethylene, tetrafluoroethylene-hexafluoropropylene copolymer and the like.

The ultra-clean and high-purity N-methyl pyrrolidone produced by the method provided by the present invention, with the purity of over 99.8%, the moisture content less than 0.02%, the content of dust particles which diameter is larger than 0.5 μm less than 10 pcs/ml, the content of single metal ion less than 1 ppb, is up to the SEMI C8 standard that is one of the chemical standards published by Semiconductor Equipment and Material International.

Comparing to the existing technology, the method the invention provided has the following advantages:
1). The pretreatment of N-methyl pyrrolidone in the invention can effectively remove γ-butyrolactone in the raw material so that the problems such as the unsteadiness of product quality and high production cost, etc. are avoided.
2) β-cyclodextrin composite membrane and 18-crown-6 composite membrane are used in the present invention to filtration which can remove metallic ions effectively. And it is simple and convenient to operate, has good separating result, and is suitable for industrial continuous production.

BRIEF DESCRIPTION OF THE DRAWING

FIG. 1 is a technical process view of the method according to the present invention for production of ultra-clean and high-purity N-methyl pyrrolidone, in which single 1 is high-purity quartz reactor, 2 is the filter, 3. is the 4A molecular sieve absorber, 4 is the first membrane filter, 5 is the second membrane filter, 6 is the rectifying tower, 7 is product fraction collector reservoir, 8 is light fraction collection tank 9 is the third membrane filter and 10 is product storage vessel.

DETAILED DESCRIPTION OF THE PREFERRED EMBODIMENTS

Embodiment 1

The pretreatment of N-methyl pyrrolidone:

350 kg industrial grade N-methyl pyrrolidone is added into the 500 L high-purity quartz reactor 1 equipped with heating unit, stirring unit, thermometer and gas distributor, the temperature is controlled at 30±5° C. and methylamine is added continuously into the N-methyl pyrrolidone by gas distributor with a velocity of flow of 5 L/min to react for 1 hour under stirring conditions the weight ratio of the methylamine and industrial grade NMP is 4:1). The N-methyl pyrrolidone is filtered in the filter 2, then dehydrated passing through 4A molecular sieve absorber of φ400×600 mm with a velocity of flow of 6 L/min at the temperature of 30 to 40° C. to obtain the pretreated NMP.

Production of ultra-clean and high-purity NMP:

The pretreated NMP is delivered into the first membrane filter 4 with β-cyclodextrin composite membrane which aperture is 0.1 μm as filter membrane and the second membrane filter 5 with 18-crown-6 composite membrane which aperture is 0.1 μm as filter membrane in order to filter at the pressure of 0.5MPa to remove the metallic ions and solid particles. The filtrate is rectified in rectifying tower 6 (volume of which is 500 L, diameter is 300 mm, height is 5000 mm) under the conditions of 80 KPa and the 120° C. temperature of the top of the tower. In the process of rectification, the light fractions are collected from the outlet at the ⅔ height of the rectifying tower with a velocity of flow of 3 to 5 L/min and stored in the light fraction collection tank (for recycling). The NMP fraction is collected from the top opening of the tower and then is condensed, and transferred into the third membrane filter 9 through ultra-pure quartz pipes to filtration to obtain product of ultra-clean and high-purity NMP. The product is stored in the ultra-pure perfluorinated product storage vessel 10.

The purity of the product is detected by the following methods: Optical Colorimetry with Platinum-Cobalt Standard Solution as standard color for chromaticity; Gas Chromatography Analysis for content of isopropyl or hydrochloride; Carl Fisher Method for water content; Gravimetric Analysis for the Residue after Evaporation; ICP-MS for cations; and ion-exchange Chromatograph Analysis for anions. And the analytical instruments are list in table 2, and the detect results are list in table 1.

Embodiment 2

The pretreatment of N-methyl pyrrolidone:

350 kg industrial grade N-methyl pyrrolidone into the 500 L high-purity quartz reactor equipped with heating unit, stirring unit, thermograph and gas distributor, at, the temperature of 35±5° C. and methylamine is added continuously into the N-methyl pyrrolidone by gas distributor with a velocity of 6 L/min to react for 1 hour under stirring conditions (the weight ratio the methylamine and industrial grade NMP is 6:1). Then the N-methyl pyrrolidone is filtered in the filter 2 at the temperature of 30 to 40° C., dehydrated passing through 4A molecular sieve absorber of φ<400×600 mm with a velocity of flow of 6 L/min at 30 to 40° C. to obtain the pretreated NMP.

Production of the ultra-dean and high-purity NMP:

The pretreated NMP is delivered into the first membrane filtration with β-cyclodextrin composite membrane with aperture of 0.2 μm to filtration at pressure of 0.5 MPa and the second membrane filtration with 18-crown-6 composite membrane under the same condition. The filtrate is delivered into the rectifying tower 6 (volume of which is 500 L, diameter is 300 mm, height is 5000 mm) and rectified under conditions of 40 KPa and 80° C. temperature of top of the tower. In the process of rectification, the light fractions are collected from the outlet at the ⅔ height of the rectifying tower with a velocity of flow of 3~6 L/min and stored in the collecting vessel (for recycling), and the NMP fraction is collected and condensated, and filtered the third using 18-crown-6 composite membrane at the pressure of 0.5 MPa. The filtrate is collected and the target product obtained.

The purity detected result according to the method of embodiment 1 is list in Table 1.

TABLE 1

Standard of N-methyl pyrrolidone and Analysis Results

| Parameter | U.M. | SEMI C8 Standard | Embodiment 1 | Embodiment 2 |
|---|---|---|---|---|
| content of NMP | % | 99.80 | 99.85 | 99.88 |
| Appearance | APHA | ≦30 | 18 | 21 |
| Content of water(H2O) | % | ≦0.03 | 0.013 | 0.018 |
| Free amine state (as CH3NH2) | ppm | ≦5 | 3 | 3 |
| Chloride (Cl) | ppb | ≦300 | 112 | 108 |
| Nitrate (NO3) | ppb | ≦400 | 235 | 250 |
| Phosphate (PO4) | ppb | ≦250 | 113 | 112 |
| Sulphate (SO4) | ppb | ≦250 | 135 | 128 |
| aluminum (Al) | ppb | ≦5 | 0.02 | 0.02 |
| antimony (Sb) | ppb | ≦10 | 5 | 3 |
| arsenic (As) | ppb | ≦10 | 5 | 5 |
| boron (B) | ppb | ≦10 | 6 | 5 |
| cadmium (Cd) | ppb | — | — | — |
| calcium (Ca) | ppb | ≦5 | 1.4 | 1.2 |
| chromium (Cr) | ppb | ≦10 | 3 | 3 |
| cobalt (Co) | ppb | — | — | — |
| copper (Cu) | ppb | ≦5 | 2.5 | 2.2 |
| glod (Au) | ppb | ≦5 | 2.4 | 2.3 |
| iron (Fe) | ppb | ≦10 | 6.2 | 6.1 |
| lead (Pb) | ppb | ≦5 | 3.5 | 3.1 |
| lithium (Li) | ppb | — | — | — |
| magnesium (Mg) | ppb | ≦5 | 3.0 | 2.8 |
| manganes (Mn) | ppb | ≦5 | 2.6 | 2.6 |
| nickel (Ni) | ppb | ≦5 | 2 | 2 |
| potassium (K) | ppb | ≦5 | 2 | 2 |
| Silver (Ag) | ppb | — | — | — |
| sodium (Na) | ppb | ≦10 | 4 | 4 |

TABLE 1-continued

Standard of N-methyl pyrrolidone and Analysis Results

| Parameter | U.M. | SEMI C8 Standard | Embodiment 1 | Embodiment 2 |
|---|---|---|---|---|
| strontium (Sr) | ppb | — | — | — |
| tin (Sn) | ppb | ≦5 | not detected | not detected |
| titanium (Ti) | ppb | ≦5 | not detected | not detected |
| vanadium (V) | ppb | — | — | — |
| zinc (Zn) | ppb | ≦10 | 6 | 5 |
| Content of dust particle(≧0.5 μm) | pcs/ml | ≦15 | 8 | 8 |

TABLE 2

The name and the type of the analysis instrument

| Instrument | Technical Indexes | Type |
|---|---|---|
| Autotitrator | <0.01% | Mettler DL50 |
| ICP-MS | detection limit <1 ppt | Agilent ICP-MS-7500S |
| Moisture Titrator | DL31 | METTLER TOLEDO |
| Double-pump liquid Chromatograph | 1525 | Waters |
| Turbidity Meter | Test limits <0.1 ppb | 2100N HACH |
| Ultraviolet Spectrophotometer | Content of Anion <20 ppb | Thermal Alpha UV-Vis |
| Laser Light Scattering Particle Detector | Content of particle (<0.1 μm) | Rion 40AF |

We were informed from the Table 1 that the ultra-clean and high-purity N-methyl pyrrolidone produced by method the present invention provided, the purity of which is over 99.8%, moisture content less than 0.02%, the content of dust particles whose diameter is larger than 0.5 μm less than 10 pcs/ml, and the content of single metal ion less than 1 ppb, is up to the SEMI C8 standard.

It should be appreciated that the above embodiments are put forward as the emulation of preferable embodiments of the invention, where the invention is not limited by them. Numerous other simplified improvements devised by a person skilled in the art without departing from the scope of the invention will fall into the scope of the present invention.

The invention claimed is:

1. A method for producing N-methyl pyrrolidone, comprising:
    feeding methylamine into N-methyl pyrrolidone to react for about 0.5 to 1.5 hours at temperatures of 5 to 20° C., and the N-methyl pyrrolidone is dehydrated by passing through a 4A molecular sieve with a velocity of flow of 5 to 7 L/min;
    providing complex composite membranes with aperture of 0.1 to 0.2 μm as filter membranes to carry out two membrane filtrations, filtrate is rectified at a pressure of 20 to 80 KPa, and fractions of 80 to 120° C. are collected from a top of a rectifying tower; the fraction is filtered third through microporous film to get a target product.

2. A method according to claim 1, wherein the weight ratio between the industrial grade N methyl pyrrolidone and methylamine is 1:2 to 1:8.

3. A method according to claim 2, wherein the weight ratio between the N-methyl pyrrolidone and methylamine is 1:3 to 1:7.

4. A method according to claim 1, wherein the light fractions are discharged with a velocity of flow 3 to 5 L/min from an outlet at ⅔ of a height of the rectifying tower.

5. A method according to claim 1, wherein a dehydration temperature is controlled at 20 to 40° C. during a process of dehydration using a 4A molecular sieve.

6. A method according to claim 1, wherein the composite membrane used in a first filtration is β-cyclodextrin composite membrane and a second is 18-crown-6 composite membrane.

7. A method according to claim 1, wherein an 18-crown-6 composite membrane is used for a third filtration.

8. The method according to claim 1, wherein the N-methyl pyrrolidone used in the feeding step is formed by a method comprising:
    heating, pressurizing and dehydrating N-methyl-4-hydroxyl butyrylamide which is produced by a reaction of γ-butyroactone with methylamine.

9. A method according to claim 1, wherein the N-methyl pyrrolidone is over 99.8% pure.

10. The method according to claim 1, wherein the N-methyl pyrrolidone has a moisture content less than 0.02%.

11. The method according to claim 1, wherein the N-methyl pyrrolidone has a content of dust particles larger than 0.5 μm of less than 10 pcs/ml.

12. The method according to claim 1, wherein the N-methyl pyrrolidone has a single metal ion content of less than 1 ppb.

13. The method according to claim 1, wherein the N-methyl pyrrolidone meets the SEMI C8 standard.

* * * * *